(12) United States Patent
Howell

(10) Patent No.: US 9,648,831 B2
(45) Date of Patent: May 16, 2017

(54) *BUGLOSSOIDES* 'FITZROY'

(71) Applicant: Philip Howell, Cambridge (GB)

(72) Inventor: Philip Howell, Cambridge (GB)

(73) Assignee: NIAB Trading, Ltd. (GB)

( * ) Notice: Subject to any disclaimer, the term of this patent is extended or adjusted under 35 U.S.C. 154(b) by 0 days.

(21) Appl. No.: 14/968,558

(22) Filed: Dec. 14, 2015

(65) Prior Publication Data

US 2016/0174502 A1  Jun. 23, 2016

(30) Foreign Application Priority Data

Dec. 18, 2014 (QZ) .................................. 2014/3490

(51) Int. Cl.
*A01H 5/10* (2006.01)
(52) U.S. Cl.
CPC ..................................... *A01H 5/10* (2013.01)

(58) Field of Classification Search
None
See application file for complete search history.

(56) References Cited

PUBLICATIONS

Surette 2013, Mol. Nutr. Food Res. 57: 748-759.*
Retief 2002, Bothalia 32: 9-13.*

* cited by examiner

*Primary Examiner* — David H Kruse
(74) *Attorney, Agent, or Firm* — Cassandra Bright

(57) ABSTRACT

A new and distinct *Buglossoides arvensis* plant named 'FitzRoy' characterized by vigorous plant growth and abundant side shoot development. Seeds are distinctively well retained on the plant. Plants flower early, between April and early June, and require vernalization to induce flowering. Seed germination rate is typically 80%. Seeds of the plant are used in the production of the oil commercially known Ahiflower oil.

Figure 1:
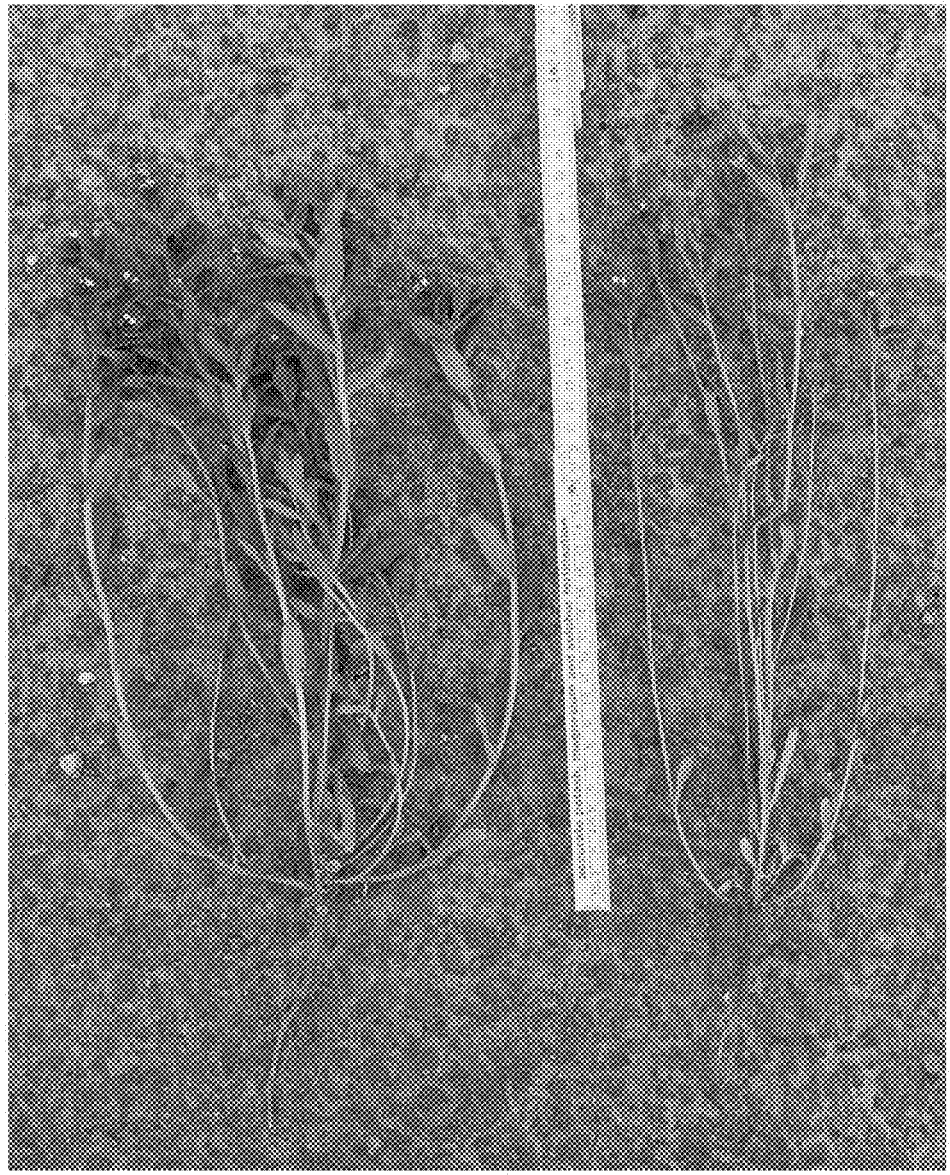

5 Claims, 3 Drawing Sheets
(3 of 3 Drawing Sheet(s) Filed in Color)

*BUGLOSSOIDES* 'FITZROY'

FIELD OF THE INVENTION

The present invention relates to a new, distinct and stable variety of *Buglossoides arvensis*, hereinafter referred it as 'FitzRoy'. The present invention relates to seeds which are the *Buglossoides arvensis* 'FitzRoy', as well as, plants and the plant parts produced by these seeds which have all the morphological and physiological characteristics of the *Buglossoides arvensis* 'FitzRoy'. The present invention also relates to methods for producing these seeds and plants of the *Buglossoides arvensis* 'FitzRoy'. Furthermore, the present invention relates to method of producing progeny *Buglossoides* plants by crossing *Buglossoides* 'FitzRoy', as either the female or seed or male or pollen parent, with another *Buglossoides* plant and selecting progeny.

BACKGROUND OF THE INVENTION

The present invention relates to a new, distinct and stable variety of *Buglossoides arvensis*, and hereinafter referred to by the variety denomination 'FITZROY'. The new *Buglossoides* 'FitzRoy' originated from the process of selection of wild collected seed, which was germinated, observed selected and subsequently self-pollinated. Germination, selection and self-crossing were made as part of a controlled breeding program by the inventor at a research greenhouse and outdoor field facility in Cambridge, England. The new variety was initially selected December 2009. The selected seed line was first multiplied in pots and an outdoor field during the summer of 2010 Cambridge, England.

*Buglossoides* is a member of the Boraginaceae family. *Buglossoides* is a genus consisting of 15 species of annual or perennial herbs, native to Europe and Asia. They grow naturally in habitats ranging from sunny scrub to rocky slopes and woodland areas.

*Buglossoides* has been identified as a potentially interesting commercial crop for seed production, with the seeds useful for oil production. The oil derived from *Buglossoides* trades under the commercial name Ahiflower oil. Research has shown that vegetable oils containing stearidonic acid (SDA) could be a dietary source of fatty acids that would be more effective in increasing tissue eicosapentaenoic acid (EPA) concentrations than are current alpha linolenic acid (ALA) containing vegetable oils. The use of SDA-containing oils in food manufacture could provide a wide range of dietary alternatives for increasing tissue EPA concentrations. Ahiflower oil is indicated to be a more efficient omega-3 alternative to flax, chia, and other ALA-rich dietary oils.

Seeds of *Buglossoides* have been approved for the above mentioned use by the FDA.

*Buglossoides* can be propagated by vegetative, asexual practices. However, this method is impractical for commercial field purposes.

Methods for cultivation and crossing of *Buglossoides* are not well known. However, it is known some varieties are suitable for Winter production, requiring vernalization, whereas some varieties will not require vernalization and produce seeds during the Summer season from Spring planting.

*Buglossoides arvensis* plants are known to produce seeds prolifically. To produce a commercial crop, it has been necessary to address the issue of variety stability, as well as seed dormancy. The inventor has developed a new variety which can be self-pollinated and reproduced true to try from seed. Plants produced by this method are uniform with respect their morphological and physiological characteristics.

A need exists for a greater variety of *Buglossoides* cultivars for commercial seed production, under a variety of environmental conditions. Additionally, a need exists for additional *Buglossoides arvensis* cultivars that can be easily propagated by seed, with consistent results. The new *Buglossoides* FitzRoy was developed through a controlled breeding program and exhibits unique, desirable and stable characteristics.

SUMMARY OF THE INVENTION

The present invention provides *Buglossoides* plant selections that can be planted in the Winter, requiring vernization to produce seeds during Summer. Additionally, plants of 'FitzRoy' typically produce many side shoots, with these side shoots starting to emerge at a lower section of the main stem than typical of *Buglossoides*. Plants begin flowering uniquely early. Germination rate of the new variety is typically around 80%, much higher than typical for *Buglossoides*. Plants are cold hardy, with improved Autumnal survival rate, observed to tolerate temperatures as low as −5° C. Additionally, plants have a superior quality to retain seeds on the plant. Agronomic performance and oil content are consistent and desirable for commercial purposes. These qualities distinguish the new cultivar from typical *Buglossoides arvensis* varieties.

These and other objectives have been achieved in accordance with the present invention which provides 'FitzRoy' as a new *Buglossoides* cultivar that is a product of a planned breeding program conducted by the inventor Phillip Howell, in Cambridge, England.

The new variety 'FitzRoy' can be produced by sexual reproduction by to produce a population of progeny plants, each of which has the combination of characteristics as herein disclosed for the new variety 'FitzRoy'.

2500 seeds which are the variety 'FitzRoy' have been deposited on 3 Nov. 2016 under the Budapest Treaty at the American Type Culture Collection (ATCC) having deposit Designation PTA-123463.

OBJECTS OF THE INVENTION

The present invention relates to seeds which produce *Buglossoides arvensis* 'FitzRoy'. The present invention also relates to *Buglossoides* plants, and parts thereof, having all the physiological and morphological characteristics of *Buglossoides arvensis* 'FitzRoy'. The present invention relates to a plant produced from seeds which are *Buglossoides arvensis* 'FitzRoy'. The present invention also relates to plant parts, such as pollen, seeds or inflorescence produced by *Buglossoides arvensis* 'FitzRoy'.

The present invention relates to a method of producing seed which are *Buglossoides arvensis* 'FitzRoy'.

The present invention also relates to a method of producing plants having all the physiological and morphological characteristics of the *Buglossoides arvensis* 'FitzRoy' comprising the steps of (a) self-pollinating *Buglossoides arvensis* 'FitzRoy' a (b) harvesting seeds produced from said cross; and (c) producing plants from said harvested seeds.

The present invention also relates to producing progeny plants from the cross of *Buglossoides arvensis* 'FitzRoy', as the female or male parent, with another *Buglossoides* plant, and selecting progeny plants from this cross.

BRIEF DESCRIPTION OF THE PHOTOGRAPHS

The patent or application file contains more than one drawing executed in color. Copies of this patent or patent application publication with color drawings will be provided by the Office upon request and payment of the necessary fees.

The accompanying photographs illustrate the overall appearance of the new *Buglossoides arvensis* 'FitzRoy' showing the colors as true as is reasonably possible with colored reproductions of this type. Colors in the photograph may differ slightly from the color values cited in the detailed botanical description which accurately describes the color of 'FitzRoy'.

FIG. 1 shows 2 plants of 'FitzRoy', grown outdoors during Winter and Spring months. The larger plant on the left is from a more widely spaced test field. The narrower plant on the right is from a densely spaced test field.

Figure 2:
Figure 3:
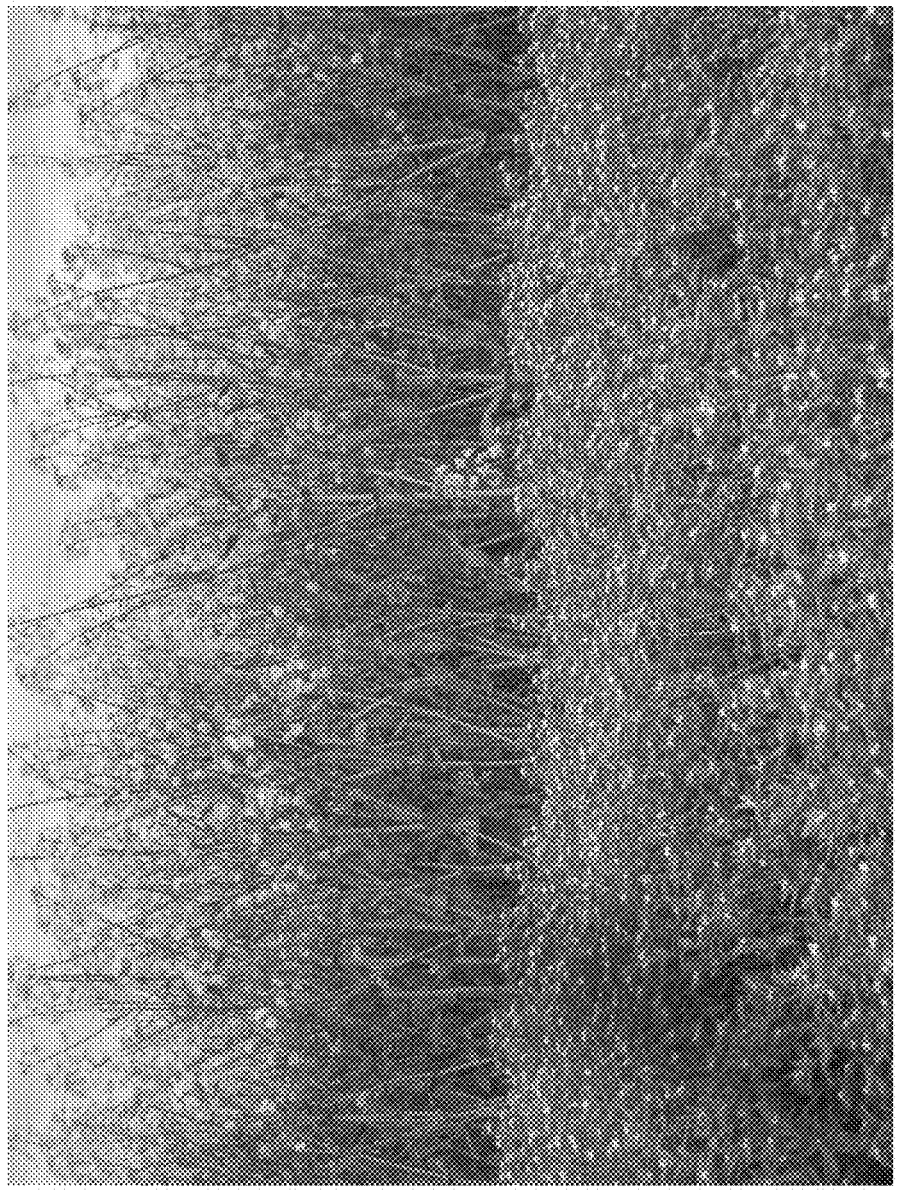

FIG. 2 illustrates a row of flower plants of 'FITZROY', identified with the label "17" in the photo FIG. 3 shows field grown plants of 'FitzRoy', grown near in front of a field of rape seed. Plants of 'FitzRoy' are the shorter plants in the foreground.

DETAILED BOTANICAL DESCRIPTION

The present invention was created by the inventor, Phillip Howell in Cambridge, England.

This invention is directed to a *Buglossoides arvensis* plant having all the morphological and physiological characteristics of the variety 'FitzRoy' produced from seeds The new *Buglossoides arvensis* 'FitzRoy' can also be produced by asexually reproducing progeny. Asexual reproduction of the new cultivar by vegetative means by cuttings was first performed in 2010, in Cambridge, England. The first 'FitzRoy' plants propagated through the use of such cuttings are maintained in Cambridge, England and have reproduced at least 5 generations. Subsequent asexual reproduction has demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'FitzRoy' which in combination distinguish this *Buglossoides* as a new and distinct cultivar:

1. Plants producing many side shoots, with side shoots emerging lower on the stem than typical of *Buglossoides arvensis*.
2. Vernalization required for seed production.
3. Plants exhibit good seed retention on plants.
4. Earlier flowering than known varieties.
5. Improved germination rate, approximately 80%.

Of the few commercial cultivars known to the present inventor, the most similar in comparison to the new *Buglossoides arvensis* 'FitzRoy' is the unnamed, unpatented *Buglossoides arvensis* maintained at Kew Gardens, hereafter referred to as 'Kew Line'. 'FitzRoy' differ from plants of 'Kew Line in the following:

1. 'FitsRoy' produces more side shoots per plant
2. 'FitzRoy' flowers somewhat earlier.
3. 'FitzRoy' produces seeds earlier.
4. 'FitzRoy' produces approximately 10% to 20% dormant seed, whereas this comparator produces approximately 80% dormant seed.
5. FitzRoy' plants are taller than plants of 'Kew Lline'.
6. 'FitzRoy has a higher seed oil content, 22% compared to 9%.
7. FITZROY' requires vernalization to initiate flowering.

'FitzRoy' can also be compared to a *Buglossoides arvensis* 'Malin', U.S. application Ser. No. 14/620,047. Plants of 'Malin' differ from plants of 'FitzRoy' in the following:

1. 'FitzRoy' requires vernalization to initiate flowering.
2. Seed size; TGW of 'FitzRoy' is typically 3 g, compared to TGW of 6.5 g of this comparator.
3. Leaf color of 'FitzRoy' is a duller grey-green color than foliage of 'Malin'.
4. Plants of 'FitzRoy' have a more pronounced seed retention at full maturity.

'FitzRoy' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

For example, substantial differences in plant height and diameter; quantity of seeds produced can occur, depending upon environmental conditions and planting density.

The aforementioned photographs, together with the following observations, measurements and values describe the new *Buglossoides* 'FitzRoy' as grown outdoors in Hertfordshire, England. Plants of 'FitzRoy' were grown outdoors in a research field with temperatures ranging from approximately 5° C. to 18° C. during the day and night temperatures ranging from −2° C. to 7° C. No artificial lighting or photoperiodic treatments were conducted. Plants were germinated at 8° C. in calcareous soil. Planting occurred during October 2014, with seed harvest around April 2015.

Color reference are made to the Royal Horticultural Society Colour Chart (RHS), 2001 edition, except where general colors of ordinary significance are used. Color values were taken under daylight conditions in a greenhouse in Cambridge, England. The age of the plants of 'FitzRoy' described is about 197 days from emergence and 211 days from sowing.

Classification;
Botanical: *Buglossoides arvensis* 'FitzRoy'
Germination: Approximately 14 to 21 days at 8° C.
Root Initiation: Approximately 21 to 30 days at approximately 6° C.
Root description: Tap root with short fibrous laterals. Grey-Brown in color, not accurately measured with RHS chart.
Plant:
Growth Habit: Erect. Herbaceous, simple to branching above, multiple stems from taproot, densely antrorse pubescent (hairs appressed).
Planting situation: Plants in the ground
Age of plant described: 197 days from emergence, 211 days from seed sown.
Height: To top of foliage: 70 cm
To top of flowers: 70 cm.
Plant Spread: 40 to 50 cm.
Growth Rate: Rapid and vigorous Spring growth, slow Winter growth.

Branching Characteristics:
Characteristics of Primary Lateral Branches:
  Diameter: 0.5 to 0.6 cm.
  Length: 35 to 50 cm.
  Color: Near RHS Green 141C.
  Texture: Antrorse pubescent
  Strength: Stiff
Internode length: 0.5 to 4 cm, length increasing with maturity.
  Foliage:
  Leaf:
  Arrangement: Alternate, sessile.
  Quantity: Approximately 10 to 15 per branch.
  Average Length: 3 to 6 cm
  Average Width: 1 to 2 cm.
  Shape of blade: Lanceolate to ovate.
  Apex: Broad acute.
  Base: Tapering, cuneate.
  Margin: Tmooth, entire.
  Texture of top surface: Densely pubescent, hairs appressed.
  Texture of bottom surface: Densely pubescent, hairs appressed.
  Aspect: Foliage tends to be curved—can angle upwards but the more mature leaves are horizontal with the tips curved down.
  Color:
  Young foliage upper side: RHS Green 141C
  Young foliage under side: RHS Green 139B
  Mature foliage upper side: RHS Green 141C
  Mature foliage under side: RHS Green 139B
  Venation:
  Type: Pinnate, under surface prominent midrib.
  Venation color upper side: RHS Green 141C
  Venation color under side: RHS Green 141C
  Petiole: sessile
  Inforescence:
Natural flowering season: April, May to early June.
Days to flowering from seed: Approximately 180 days
Inflorescence and flower type and habit: Monochasial cyme.
Rate of flower opening: 4 to 10 days from bud to fully opened flower.
Flower Longevity on Plant: Average 7 days, longer in cool weather, shorter if warm.
Persistent or Self-Cleaning: Self-Cleaning
Bud:
  Shape: Spherical
  Length: 0.3 cm
  Diameter: 0.2 cm
  Color: RHS White 155C
Flower size:
  Diameter: 0.4 cm.
  Length: 0.5 cm.
Petals:
  Length: 0.2-0.3 cm.
  Diameter: 0.2 cm
  Quantity: 5
  Texture: smooth
  Apex: round, obtuse.
  Color: When opening:
    Upper surface: RHS White 155A
    Lower surface: RHS White 155B
    Fully opened:
    Upper surface: RHS White 155A
    Lower surface: RHS White 155B
    Ageing/Fading:
    Upper surface: RHS White 155D
    Lower surface: RHS White 155D
Floral Tube:
  Length: 0.3-0.4 cm.
  Diameter: 0.1 cm
  Texture:
    Inner: Pubescent
    Outer: Pubescent
  Color: When opening:
    Inner surface: Top of tube RHS White 155A. Base of tube RHS Greyed-Green 189A
    Outer surface: RHS White 155A. Base of tube RHS Greyed-Green 189A
    Fully opened:
    Inner surface: RHS White 155A. Base of tube RHS Greyed-Green 189A
    Outer surface: RHS White 155A base of tube RHS Greyed-Green 189A
    Ageing/Fading:
    Inner surface: RHS White 155C. Base of tube RHS Greyed-Green N189A
    Outer surface: RHS White 155C. Base of tube RHS Greyed-Green N189A
Sepals:
  Quantity per flower: 5
  Shape: linear, acuminate
  Length: 0.6-0.7 cm
  Width: 0.1 cm
  Apex: pointed acuminate
  Base: cuneate
  Margin: smooth, entire
  Texture: Pubescent
  Color: RHS Green 136B.
Peduncle:
  Length: 1 to 2.5 cm
  Color: RHS Green 136B.
  Strength: Strong—becomes woody as seeds ripen
  Angle: Straight and almost upright—vertical.
Pedicel:
  Length: 0.1 cm.
  Diameter: 0.1 cm.
  Color: RHS Green 136B.
Fragrance: none observed
  Reproductive Organs:
  Stamens:
  Number: 5
  Filament length: Less than 0.1 mm
Anthers:
  Shape: Dorsifixed, parallel sacks with a groove between
  Length: 0.1 mm
  Color: RHS Greyed yellow 161 (too small to exactly specify under normal light)
Pollen:
  Color: RHS White NN155 (too small to specify under normal light)
  Quantity: Abundant
Pistil:
  Number: 1
  Length: 0.1 cm
  Style:
    Length: between 0.05 and 0.1 cm
    Color: RHS Greyed green (too small to specify under normal light)
  Stigma:
    Shape: lobed
    Color: RHS Greyed green (too small to specify under normal light)

SEED/FRUIT: Typical Thousand Grain weight near 3 g, having an average population range of 2.4 to 3.1 g.

Seed size: Average width: 1.7 mm
Average length: 2.5 mm

Oil Content: Approximately 22%.

DIESASE/PEST RESISTANCE: Good resistance to invertebrate pests, some susceptibility to powder mildew during late season under stress conditions.

Temperature tolerance: Low temperature tolerance to −5° C. from expanded cotyledon stage.

I claim:

1. A *Buglossoides arvensis* plant named 'FitzRoy', representative seed deposited at the American Type Culture Collection (ATCC) having deposit Designation PTA-123463.

2. A *Buglossoides arvensis* seed that produces the plant of claim 1.

3. A plant part obtained from the *Buglossoides arvensis* plant of claim 1.

4. A method of producing *Buglossoides arvensis* progeny comprising the steps of (a) crossing a *Buglossoides arvensis* plant named 'FitzRoy', representative seed deposited at the American Type Culture Collection (ATCC) having deposit Designation PTA-123463, as a female or male parent with another *Buglossoides arvensis* plant, and (b) selecting progeny.

5. The method according to claim 4, wherein the second *Buglossoides arvensis* plant is 'FitzRoy'.

* * * * *